United States Patent [19]
Röhlcke et al.

[11] Patent Number: 5,326,259
[45] Date of Patent: *Jul. 5, 1994

[54] MARKED ORTHODONIC AID AND METHOD OF MANUFACTURING

[75] Inventors: Friedrich-Wilhelm Röhlcke, Kämpfelbach-Bilfingen; Friedrich Sernetz, Pforzheim, both of Fed. Rep. of Germany

[73] Assignee: Dentaurum J.P. Winkelstroeter KG, Ispringen, Fed. Rep. of Germany

[*] Notice: The portion of the term of this patent subsequent to Aug. 24, 2010 has been disclaimed.

[21] Appl. No.: 48,811

[22] Filed: Apr. 16, 1993

Related U.S. Application Data

[63] Continuation of Ser. No. 348,039, Apr. 13, 1989, Pat. No. 5,238,402.

[30] Foreign Application Priority Data

Aug. 14, 1987 [DE] Fed. Rep. of Germany ....... 3727102

[51] Int. Cl.⁵ ................................................ A61C 3/00
[52] U.S. Cl. ......................................................... 433/8
[58] Field of Search ................... 433/2, 3, 4, 8, 9, 10, 433/11, 12, 13, 14, 15, 16, 17, 23; 29/160.6

[56] References Cited

U.S. PATENT DOCUMENTS

| | | | |
|---|---|---|---|
| 2,759,265 | 8/1956 | Johnson | 433/13 |
| 4,120,090 | 10/1978 | Kesling | 433/23 |
| 4,304,981 | 12/1981 | Gappa | 219/121.66 |
| 4,626,209 | 12/1986 | Tsai et al. | 433/9 |

FOREIGN PATENT DOCUMENTS 0085484 8/1983 European Pat. Off.

Primary Examiner—John J. Wilson
Attorney, Agent, or Firm—Leydig, Voit & Mayer, Ltd.

[57] ABSTRACT

In order to so improve a metallic orthodontic aid having an optically visible marking area that the marking is easy to apply and is also visible up to a definable number of recycling process cycles, it is proposed that the marking area be a surface of an additionally produced layer with a remelt structure.

15 Claims, 1 Drawing Sheet

MARKED ORTHODONTIC AID AND METHOD OF MANUFACTURING

This is a continuation of copending application(s) Ser. No. 07/348,039, filed on Apr. 13, 1989, now U.S. Pat. No. 5,238,402.

Field of the Invention

The invention relates to a metallic orthodontic aid with an optically visible marking area.

Background of the Invention

The invention further relates to a method of applying to metallic orthodontic aids surface marking areas which are optically visible.

On metallic orthodontic aids such as, for example, brackets, bands, buccal tubes etc., it is necessary to apply markings in order to clearly identify their orientation and allocation to individual types of teeth.

So far it is known to mark such orthodontic aids by, for example, a layer of color being applied or a mechanical identification, for example, in the form of a notch, being produced in the region of the marking area.

After use, the orthodontic aids may be made fit for use again by recycling processes. In these recycling processes, firstly the adhesive by means of which these were attached to the teeth is burned off, for example, pyrolitically, and secondly the entire orthodontic aid is subjected, for example, to electrolytic surface treatment in order to reproduce the original shining surface.

When orthodontic aids with color markings are subjected to such a recycling process, these color markings are later no longer visible. This has the advantage that it is proof that this aid has been subjected to a recycling process but also the disadvantage that this orthodontic aid then no longer bears any kind of identification and hence is no longer clearly identifiable.

The markings in the form of mechanically produced identifications withstand one or even several recycling processes but from these it is not possible to ascertain whether the respective orthodontic aid was subjected to a recycling process or not.

Furthermore, the markings in the form of mechanically produced identifications have the disadvantage that in comparison with color markings, they require a great deal of machine expenditure during manufacture.

SUMMARY OF THE INVENTION

The object underlying the invention is, therefore, to so improve an orthodontic aid of the generic kind that the marking is easy to apply and is also visible up to a definable number of recycling process cycles.

This object is achieved in accordance with the invention with an orthodontic aid of the kind described at the beginning by the marking area being a surface of an additionally produced layer with a remelt structure.

A layer with a remelt structure within the meaning of the inventive solution is to be understood as a layer in the metallic aid which is produced by melting a surface region of a molded or reshaped or otherwise manufactured metallic aid and the metallographic structure of which differs from the structure of the original metallic aid.

Such a layer with a remelt structure has the advantage of not becoming detached during the individual recycling process cycles but of being worn away substantially to the same extent as the remaining surface of the orthodontic aid. On the other hand, such a layer with a remelt structure can be produced with a defined thickness and, therefore, the number of recycling process cycles which this layer is to withstand can be fixed by the thickness of the layer with a remelt structure.

Particularly in view of manufacturing simplicity, it is advantageous for the layer with a remelt structure to be formed from the material of the orthodontic aid so application of an additional material can be dispensed with and only the orthodontic aid itself must undergo melting.

In order to make the optical difference from the remaining surface regions of the orthodontic aid particularly distinct, it has proven useful for the layer with a remelt structure to be roughened on the surface and, in particular, the layer with a remelt structure is conceived of as exhibiting a crater-like surface.

Furthermore, a distinct optical difference from the remaining surface regions of the orthodontic aid is achievable by the layer with a remelt structure exhibiting reaction products of the metal with an ambient medium. In the simplest case, these reaction products are metal oxides which result from the layer with a remelt structure being produced in the presence of air. On the other hand, it is, however, also possible to produce the layer with a remelt structure in the presence of other media and to thereby achieve an even more characteristic tempering color caused by the respective reaction products.

As previously stated above, the layer with a remelt structure offers the possibility of fixing the number of recycling process cycles withstood by the marking by variation of the thickness.

Accordingly, in the simplest case, provision is made for the layer with a remelt structure to exhibit a constant thickness, i.e., penetration depth, into the respective surface region of the orthodontic aid. In this case, the number of recycling process cycles after which the layer with a remelt structure is worn away is fixable by the thickness alone.

It is, however, likewise possible for the layer with a remelt structure to exhibit a defined variable thickness so that, for example, after each process cycle the marking area becomes smaller due to worn away portions of the layer with a remelt structure and hence the number of process cycles through which such an orthodontic aid has already gone is provable.

Furthermore, it is likewise possible for the layer with a remelt structure to exhibit a step-wise varying thickness so the marking area becomes smaller by a previously determinable region after, for example, one recycling process cycle.

In all of these embodiments relating to the thickness of the layer with a remelt structure, provision is made within the scope of the inventive solution for the thickness to be a multiple, in particular, an integral multiple of a layer of material worn away from the surface of the orthodontic aid in one recycling process cycle.

A further object underlying the invention is to provide a method which is as simple as possible for applying optically visible marking areas of the generic kind.

This object is achieved in accordance with the invention in a method of the kind described at the beginning by a layer with a remelt structure being produced in the region of the marking area.

This layer with a remelt structure could be produced by, for example, applying prior to the melting procedure an additional material which then unites by means of the melting with a surface of the orthodontic aid. It is, however, considerably easier for the layer with a remelt structure to be produced by surface melting of the aid so no additional application of material is required and the aid having, for example, polished surfaces, is only melted in that region in which the marking area is to be produced.

In particular, in order to improve the optical differentiation of such a layer with a remelt structure from the remaining surface of the aid it is advantageous for the layer with a remelt structure to be produced by melting which differs in intensity from point to point, thereby further increasing the surface roughness in the region of the melting.

In the inventive method, it has proven particularly advantageous for the layer with a remelt structure to be produced by a laser beam or an electron beam or a microplasma because all possible forms of markings are producible in a simple manner with these and, in addition, these are best suited for manufacturing layers with a remelt structure having defined thicknesses.

In order to achieve an optical difference which is as clearly visible as possible between a polished surface of the orthodontic aid and the layer with a remelt structure, it has proven advantageous for the layer with a remelt structure to be produced in the presence of a medium which reacts with the metal so a special color can be imparted to it by appropriate choice of medium. In the simplest embodiment of this method, the layer with a remelt structure is produced in the presence of air so the metal reacts with the air and the reaction products exhibit the typical tempering colors known from incandescence.

As previously stated in conjunction with the advantages of the inventive method, the latter provides the possibility of producing markings which are not worn away to a stronger degree than the remaining surface of the orthodontic aid in the individual recycling process cycles. For this reason, it is advantageous within the scope of the invention for the layer with a remelt structure to be produced with a thickness which is a multiple, in particular, an integral multiple of the layer thickness worn away in one recycling process cycle.

Hence it is, for example, possible with a layer with a remelt structure having a constant thickness to select it such that it is completely worn away and thus no longer visible after one or after several recycling process cycles.

With a layer with a remelt structure having a varying thickness, it is, however, also possible for the marking area to decrease in size after each recycling process cycle in accordance with the completely worn away portion of the layer with a remelt structure so each individual marking cycle is thereby provable. In this connection, it is particularly advantageous for the layer with a remelt structure to be produced with step-wise increasing thickness, with the change in thickness in the case of one step corresponding to the layer thickness worn away in one recycling process cycle so the marking area becomes smaller in a step-wise manner after each recycling process cycle.

The inventive method can, however, also be used with advantage to produce a marking which withstands all of the recycling process cycles to which an orthodontic aid can be subjected within the scope of its service life. Here, too, the advantage that layers with a remelt structure having a defined thickness are producible with the inventive method has a positive effect because, in this case, the thickness of the layer with a remelt structure may be selected such that it is larger in all regions than the sum of the layer thicknesses worn away in recycling process cycles during the service life of such an aid so the marking area continues to have the same size after each recycling process cycle.

DESCRIPTION OF THE INVENTION

Further features and advantages of the invention are the subject of the following description and the drawings of some embodiments. The drawings show:

FIG. 1 a perspective view of a first embodiment of an aid;

FIG. 2 a section along line 2—2 in FIG. 1; and

FIG. 3 a section similar to FIG. 2 in a second embodiment.

DETAILED DESCRIPTION OF THE PREFERRED EMBODIMENT

Figure 1:
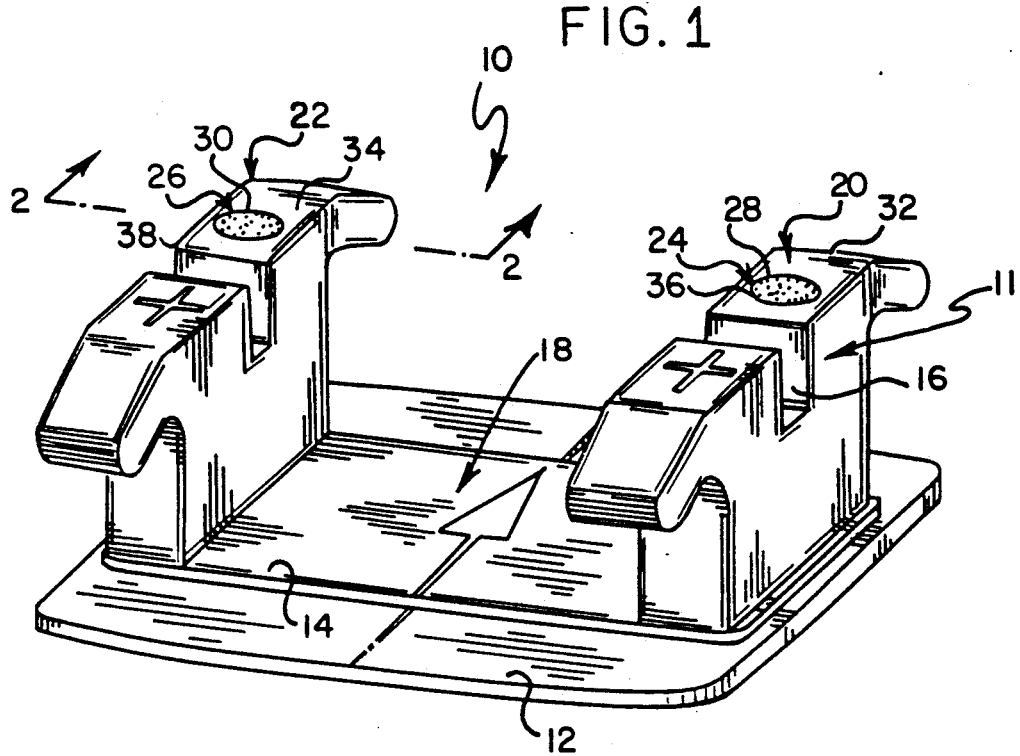

A first embodiment of an inventive aid designated in its entirety 10 in FIG. 1 comprises a bracket 11 the base of which is welded to a retention base 12. The bracket 11 is normally profiled, the type of profile apparent from FIG. 1 being typical. Longitudinal grooves 16 and transverse grooves 18 are usually disposed in such a bracket profile. This results in small areas on the front sides 20, 22 facing away from the base 14 with markings 24, 26 disposed on them. Markings in the region of the transverse groove 18 are likewise possible.

Figure 2:
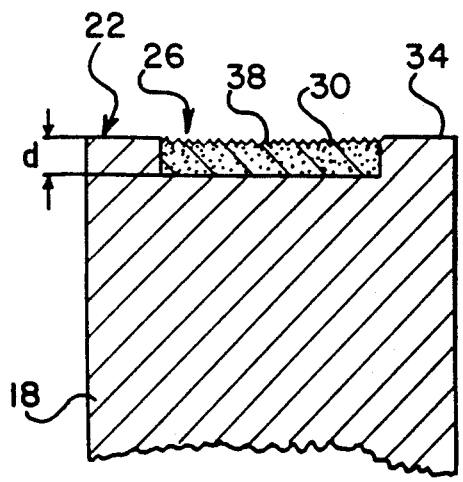

These point-type markings 24 and 26, respectively, as shown in section in FIG. 2, are layers with a remelt structure 28 and 30, respectively, which extend with a thickness d from a surface 32 and 34, respectively, of the respective front side 20 and 22, respectively, in the direction of the retention base 12 into the bracket 11. In the region of these layers with a remelt structure 28 and 30, respectively, the metal from which the bracket 11 is made was heated above the melting point by a laser beam so the structure, for example, when heated in air, exhibits the tempering color which is characteristic of the metal heated to incandescence and which results from the chemical reaction of the metal heated above the melting point with the air. Furthermore, a surface 36 and 38, respectively, of the layer with a remelt structure 28 and 30, respectively, is no longer smoothly polished like the surfaces 32 and 34, respectively, of the front sides 20 and 22, respectively, but rough, which is achievable, for example, by the laser beam being moved over the surface in a grating-type manner during manufacture of the layers with a remelt structure 28 and 30, respectively.

The thickness d of the layer with a remelt structure 28 and 30, respectively, depends on the energy supplied in point-type configuration to the respective surface region upon which the laser beam impinges. Accordingly, greater laser beam energy or longer dwell time of the laser beam on the respective point results in a greater thickness d of the layer with a remelt structure and the latter, therefore, extends further into the interior of the respective bracket wing 16 and 18, respectively.

In the embodiment illustrated in FIG. 2, the thickness d is chosen constant across the entire layer with a remelt structure 28 and 30, respectively, and, therefore, when surface wearing-away of the layer with a remelt structure 28 and 30, respectively, occurs in conjunction with a recycling process cycle, the range of the respectively visible surface 36 and 38, respectively, of the respective marking 24 and 26, respectively, is not altered.

Figure 3:
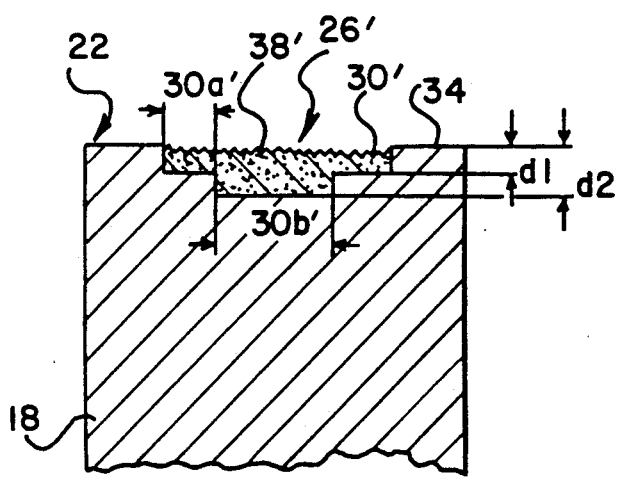

In contrast with this, the second embodiment, illustrated in FIG. 3, shows a marking 26' with step-shaped cross-section of the layer with a remelt structure 30'.

This layer with a remelt structure 30' is divided up into an outer region 30a' having the thickness d 1 and an inner region 30b' having the thickness d 2 which is, for example, a multiple of the thickness d 1.

In this embodiment, when the layer with a remelt structure 30' is worn away, for example, after several recycling process cycles, by the amount of layer thickness d 1, the size of the surface 38' has then altered because the wearing-away has caused the outer regions 30a' of the layer with a remelt structure to become worn away and only the inner regions 30b' with a thickness of d 2 minus d 1 are left. Thus, the marking 26' is still present but has a smaller surface which corresponds to the inner region 30b'.

The thickness d 1 of the layer with a remelt structure 30' may be so selected that it is worn away, for example, after two recycling process cycles and so the number of recycling process cycles which the respective bracket has undergone is immediately discernible from the size of the surface 38'.

In accordance with the invention, the thicknesses d, d 1, d 2 of the layers with a remelt structure 30, 30' are chosen in the range of approximately 0.1 $\mu$m to 0.5 $\mu$m. A layer with a remelt structure 30, 30' having a thickness d, d 1, d 2 of 0.1 $\mu$m, as a rule, withstands approximately one recycling process cycle and is worn away after such a recycling process cycle. In contrast, a layer with a remelt structure 30, 30' having a thickness d, d 1, d 2 of approximately 0.5 $\mu$m can be termed as recycling-resistant because such a layer would only be worn away after approximately five recycling process cycles and, as a rule, five recycling process cycles are not conceivable for a bracket.

The above description of the marking of an inventive bracket applies in like manner to the markings of bands and buccal tubes.

We claim:

1. An orthodontic aid comprising a metallic body having an outer surface with indicia consisting essentially of a remelt structure of the same material as said metallic body, the remelt structure of the marking area indicia having a predetermined thickness providing a permanent wear characteristic.

2. The metallic orthodontic air according to claim 1 wherein said predetermined thickness of said remelt structure is at least about 0.5 $\mu$m to provide said permanent wear characteristic.

3. The metallic orthodontic aid according to claim 2 wherein said remelt structure has a rougher surface than said outer surface.

4. A method of producing identifying indicia on an orthodontic aid, comprising the steps of providing a preformed metallic orthodontic body having an outer surface, and remelting a portion of said outer surface to form indicia having a predetermined thickness measured from said outer surface to provide a permanent marking on said body.

5. The method according to claim 4 wherein said remelting step consists essentially of heating said orthodontic body under ambient atmospheric conditions.

6. The method according to claim 5 wherein said remelting is performed to a thickness of at least 0.5 $\mu$m.

7. The method according to claim 6 wherein said remelting step is performed by a laser which heats the surface of the orthodontic body above its melting temperature for a sufficient time to effect said remelting to said thickness.

8. In an orthodontic appliance having a metallic body with an outer surface having indicia, the improvement wherein said indicia consists essentially of a remelt structure formed in said surface to a predetermined thickness for providing a permanent marking on the orthodontic appliance.

9. The orthodontic appliance according to claim 8, wherein said predetermined thickness is at least about 0.5 $\mu$m.

10. The orthodontic appliance according to claim 8 wherein said outer surface of said body is smooth and said remelt structure is rough.

11. In a method of marking a metallic orthodontic appliance, wherein a pre-formed metallic body having a smooth outer surface is provided, the improvement comprising the steps of locally heating said outer surface to remelt the metallic body to a predetermined thickness, and advancing said local heating relative to said surface to remelt in the form of a legible marking the outer surface of the body.

12. The method according to claim 11 wherein said local heating is performed for a time sufficient to remelt said body to a thickness of at least about 0.5 $\mu$m and to effect a surface finish which is rougher than the surface finish of the body.

13. The method according to claim 12 wherein said local heating is effected by means of a laser beam.

14. A metallic orthodontic aid comprising a metallic body having an outer surface and a marking on the outer surface, the marking comprising a remelt structure made of the same material as the outer surface, and the remelt structure of the marking having a wear characteristic which is substantially the same as that of the remainder of the outer surface.

15. A method of producing an optically visible surface marking on a metallic orthodontic aid, the method comprising the steps of providing a metallic orthodontic aid having an outer surface, treating a portion of the outer surface to produce a remelt structure as a marking on the outer surface, the treating step providing a remelt structure having a wear characteristic which is substantially the same as that of the remainder of the outer surface.

* * * * *